US012130255B2

(12) United States Patent
Cooks et al.

(10) Patent No.: US 12,130,255 B2
(45) Date of Patent: *Oct. 29, 2024

(54) HIGH-THROUGHPUT LABEL-FREE ENZYMATIC BIOASSAYS USING DESI-MS

(71) Applicant: Purdue Research Foundation, West Lafayette, IN (US)

(72) Inventors: Robert Graham Cooks, West Lafayette, IN (US); Nicolás M. Morato, West Lafayette, IN (US); Dylan T. Holden, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,827

(22) Filed: Dec. 20, 2022

(65) Prior Publication Data

US 2023/0324335 A1    Oct. 12, 2023

Related U.S. Application Data

(63) Continuation of application No. 17/846,923, filed on Jun. 22, 2022, now Pat. No. 11,531,005, which is a continuation of application No. 17/193,120, filed on Mar. 5, 2021, now Pat. No. 11,397,166.

(60) Provisional application No. 63/022,715, filed on May 11, 2020.

(51) Int. Cl.
*G01N 27/64*    (2006.01)
*G01N 27/622*    (2021.01)
*G01N 27/626*    (2021.01)
*H01J 49/04*    (2006.01)

(52) U.S. Cl.
CPC ......... *G01N 27/622* (2013.01); *G01N 27/626* (2013.01); *G01N 27/64* (2013.01); *H01J 49/0409* (2013.01)

(58) Field of Classification Search
CPC .... G01N 27/622; G01N 27/626; G01N 27/64; G01N 2500/02; G01N 33/573; G01N 33/6851; H01J 49/0409; H01J 49/142; H01J 49/165
USPC ................................................. 250/281, 282
See application file for complete search history.

(56) References Cited

U.S. PATENT DOCUMENTS

| | | | |
|---|---|---|---|
| 5,644,131 A | 7/1997 | Hansen | |
| 6,838,666 B2 | 1/2005 | Ouyang et al. | |
| 7,335,897 B2 | 2/2008 | Takats et al. | |
| 9,184,036 B2 | 11/2015 | Cooks et al. | |
| 9,460,904 B1 * | 10/2016 | Greving | H01J 49/0418 |
| 11,501,440 B2 * | 11/2022 | Weisenfeld | G06T 3/0075 |
| 2003/0164449 A1 | 9/2003 | Heinzle et al. | |
| 2008/0156985 A1 | 7/2008 | Venter et al. | |
| 2017/0314058 A1 * | 11/2017 | Northen | C12Q 1/26 |

(Continued)

OTHER PUBLICATIONS

Bonner, 1977, The Cylindrical Ion Trap, International Journal of Mass Spectrometry and Ion Physics, 24(3):255-269.

(Continued)

*Primary Examiner* — Michael Maskell
(74) *Attorney, Agent, or Firm* — Brown Rudnick LLP; Adam M. Schoen

(57) ABSTRACT

The invention generally relates to high-throughput label-free enzymatic bioassays using desorption electrospray ionization-mass spectrometry (DESI-MS).

9 Claims, 19 Drawing Sheets

(56) References Cited

U.S. PATENT DOCUMENTS

2020/0381238 A1    12/2020    Cooks et al.

OTHER PUBLICATIONS

Cooks, 2011, New ionization methods and miniature mass spectrometers for biomedicine: DESI imaging for cancer diagnostics and paper spray ionization for therapeutic drug monitoring, Faraday Discussions, 149:247-267.

Eberlin, 2011, Desorption electrospray ionization mass spectrometry for lipid characterization and biological tissue imaging, Biochimica Et Biophysica Acta, 1811(11):946-960.

Gao, 2006, Handheld Rectilinear Ion Trap Mass Spectrometer, Anal. Chem., 78:5994-6002.

Gao, 2008, Design and Characterization of a Multisource Hand-Held Tandem Mass Spectrometer, Z. Anal. Chem, 80(19):7198-7205.

Hagar, 2002, A new linear ion trap mass spectrometer, Rapid Communications in Mass Spectrometry, 16(6):512-526.

Haslam, 2021, The Evolution of MALDI-TOF Mass Spectrometry toward Ultra-High-Throughput Screening: 1536-Well Format and Beyond, 21(2):176-186.

Hendricks, 2014, Autonomous in-situ analysis and real-time chemical detection using a backpack miniature mass spectrometer: concept, instrumentation development, and performance, Anal Chem, 86:2900-2908.

Hou, 2011, Sampling wand for an ion trap mass spectrometer, Anal Chem., 83:1857-1861.

International Search Report and Written Opinion issued in International Application No. PCT/US2021/021017, date of mailing: Dec. 5, 2021, 13 pages.

Li, 2014, Miniature Ambient Mass Analysis System, Anal. Chem., 86:2909-2916.

Oreland, 1987, Monoamine Oxidase Enzymes, Journal of Neural Transmission, Retrieved from the Internet: ,URL: https://www.google.com/books/edition/monoamine_Oxidase_Enzymes/Wql3BQAAQBAJ?hl=en&gbpv=1&dq=Enzymatic+reactions+compound+inhibitor%22restart+the+reaction%22&pg=PT40&printsec=frontcover>.

Sokol, 2011, Miniature mass spectrometer equipped with electrospray and desorption electrospray ionization for direct analysis of organics from solids and solutions, Int J Mass Spectrom, 306(2-3):187-195.

Takats, 2004, Mass Spectrometry Sampling Under Ambient Conditions with Desorption Electrospray Ionization, Science, 306:471-473.

Extended European Search Report issued in European Application No. 21813604.2, date of mailing: Jun. 4, 2024, 10 pages.

Jiang, 2015, Droplet Spray Ionization from a Glass Microscope Slide: Real-Time Monitoring of Ethylene Polymerization, Analytical Chemistry, 87(16):8057-8062.

Kuster, 2013, Interfacing droplet microfluidics with matrix-assisted laser desorption/ionization mass spectrometry: label-free content analysis of single droplets, Analytical chemistry, 85:1285-1289.

Morato, 2020, High-Throughput Label-Free Enzymatic Assays Using Desorption Electrospray-Ionization Mass Spectrometry, Angewandte Chemie International Edition, 59(46):20459-20464.

Yan, 2017, Ambient Ionization Mass Spectrometry Measurement of Aminotransferase Activirty, Journal of the American Society for Mass Spectrometry, 28(6):1175-1181.

* cited by examiner

HIGH-THROUGHPUT LABEL-FREE ENZYMATIC BIOASSAYS USING DESI-MS

RELATED APPLICATION

The present application is a continuation of U.S. nonprovisional application serial number 17/846,923, filed Jun. 22, 2022, which is a continuation of U.S. nonprovisional application serial number 17/193,120, filed Mar. 5, 2021, which claims the benefit of and priority to U.S. provisional patent application serial number 63/022,715, filed May 11, 2020, the content of each of which is herein incorporated by reference in its entirety.

GOVERNMENT INTEREST

This invention was made with government support under W911NF-16-2-0020 awarded by the Army Research Office on behalf of the Defense Advanced Projects Research Agency. The government has certain rights in the invention.

FIELD OF THE INVENTION

The invention generally relates to high-throughput label-free enzymatic bioassays using desorption electrospray ionization-mass spectrometry (DESI-MS).

BACKGROUND

Enzymes are important drug targets. Many marketed drugs today function through inhibition of enzymes mediating disease phenotypes. Enzyme inhibitors are an important class of pharmacological agents. Often these molecules are competitive, reversible inhibitors of substrate binding.

To that end, enzyme assays are important tools for measuring cellular activity and for monitoring enzyme proteins. Measurement of enzyme kinetics provides crucial information on the mechanisms of enzyme catalysis and on the interactions of enzymes with substrates, inhibitors, drugs, and drug candidates.

SUMMARY

The invention provides a high-throughput platform that combines a set of interrelated methods in which mass spectrometry methods may be used to create droplets and thin films in which reactions occur (optionally accelerated reactions in certain embodiments), while simultaneously or subsequently using mass spectrometry to analyze the product distribution in the droplets and/or thin films. This platform has broad applicability to many different chemical and biological systems. In embodiments described herein, this platform is applied to enzymatic reactions and enzymatic bioassays.

In certain aspects, the invention provides methods for monitoring an enzymatic reaction. These methods involve preparing a plurality of discrete spots on a substrate. In certain embodiments, each of the plurality of discrete spots is from a different time point in an enzymatic reaction. In other embodiments, each of the discrete spots may be from the same time point for different reactions with different inhibitor/reactivator/substrate/enzyme concentrations. For example, a set up based on a same end point would be more common for drug discovery, whereas a set-up based on different time points would be common for biochemical studies and enzyme characterization.

Each of the discrete spots may comprise a substrate and a product(s) of the enzymatic reaction. The methods then involve directing sequentially a discharge from an ionization source onto each of the plurality of discrete spots to sequentially desorb the substrate and/or product(s) from each of the discrete spots and sequentially generate ions of the substrate and/or product(s) from each of the discrete spots that enter a mass spectrometer, and analyzing sequentially the ions of the substrate and/or product(s) from each of the discrete spots in the mass spectrometer to thereby monitor the enzymatic reaction. As mentioned above, in certain embodiments, each of the plurality of discrete spots may be from a different time point in an enzymatic reaction that has been stopped prior to the preparation step. In other embodiments, each of the plurality of discrete spots is from a different time point in an enzymatic reaction that has not been stopped prior to the preparation step. In certain embodiments a compound is added to the reaction mixture to serve as an internal standard for quantitation.

In other aspects, the invention provides methods for monitoring an enzymatic reaction that involve preparing a plurality of discrete spots on a substrate. In certain embodiments a compound is added to the reaction mixture to serve as an internal standard for quantitation. Each of the discrete spots may comprise a substrate and a product of the enzymatic reaction. Such methods additionally involve directing sequentially a discharge from an ionization source onto each of the plurality of discrete spots to sequentially desorb the substrate and/or product(s) from each of the discrete spots and sequentially generate ions of the substrate and/or product(s) from each of the discrete spots that enter a mass spectrometer, obtaining sequentially ion intensities of the ions of the substrate and/or product(s) from each of the discrete spots in the mass spectrometer, and converting ion intensities of the ions of the substrate and/or product(s) from each of the discrete spots into concentration ratios of the substrate and product(s) by applying a calibration curve, thereby monitoring the enzymatic reaction. In certain embodiments, each of the plurality of discrete spots is from a different time point in an enzymatic reaction that has been stopped prior to the preparation step. In other embodiments, each of the plurality of discrete spots is from a different time point in an enzymatic reaction that has not been stopped prior to the preparation step. In certain embodiments, the methods measure not necessarily the ratio of product and substrate but the ratio of either of those and an internal standard.

In certain embodiments of the above methods, the ionization source is a desorption electrospray ionization (DESI) probe and the discharge is a DESI spray.

In certain embodiments of the above methods, a subset of each of the plurality of the discrete spots further comprises a same test compound. In such embodiments, the method further comprises determining whether the test compound inhibits the enzymatic reaction based on the monitoring of the progress of the enzymatic reaction. In such embodiments, the method further comprises determining how completely the test compound inhibits the enzymatic reaction based on the monitoring of the progress of the enzymatic reaction. In such embodiments, the enzymatic reaction is associated with a physiological condition and determining how completely the test compound inhibits the enzymatic reaction determines whether the test compound should be considered for development into a drug to treat the condition.

In other embodiments, a subset of each of the plurality of the discrete spots further comprises an inhibitor of an enzyme of the enzymatic reaction and a test compound. In such embodiments, the method further comprises determining whether the test compound can counteract the inhibitor and re-start the enzymatic reaction. In such embodiments, the method further comprises determining how completely the test compound counteracts the inhibitor and how completely the enzymatic reaction is re-started based on the monitoring of the progress of the enzymatic reaction. In such embodiments, determining how completely the test compound counteracts the inhibitor and how completely the enzymatic reaction is re-started determines whether the test compound should be considered for development into a drug that counteracts the inhibitor.

BRIEF DESCRIPTION OF THE DRAWINGS

FIG. 13 panel B shows that the log-transformed data shows the expected linear behavior (R2=0.996).

DETAILED DESCRIPTION

Figure 1:
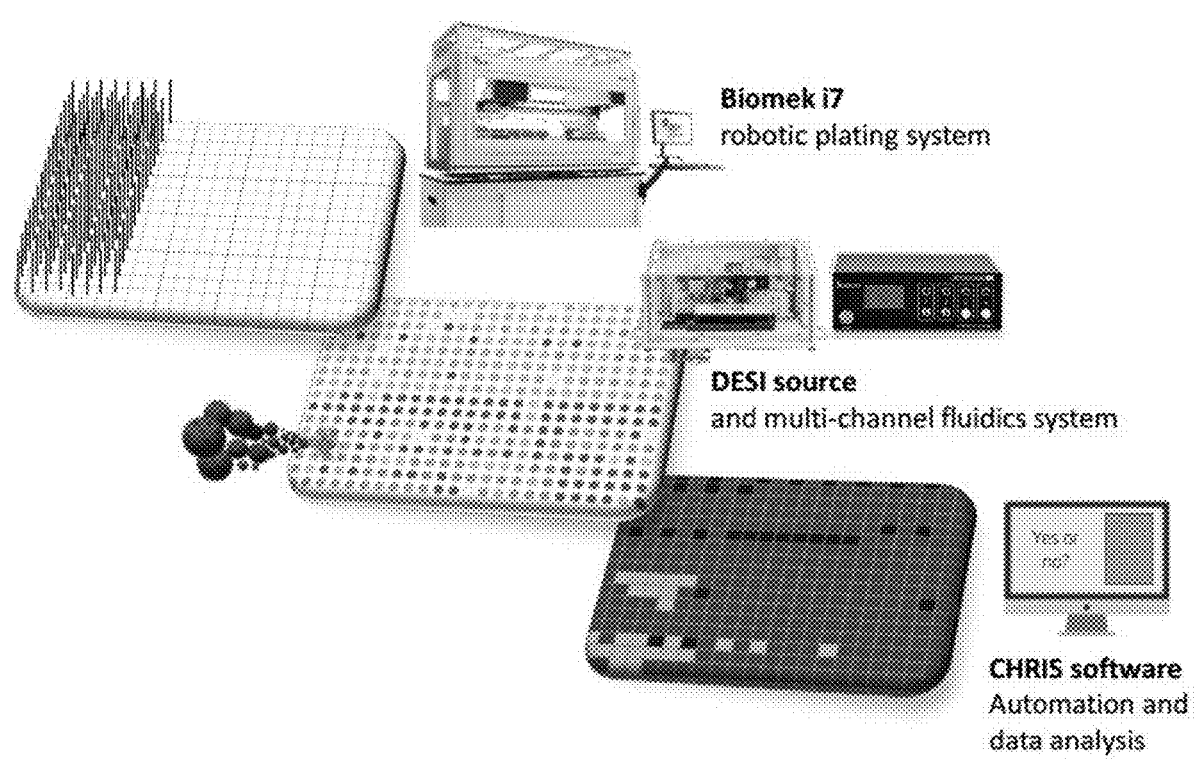
FIG. 1 describes an overview of the high-throughput platform.
Figure 2:
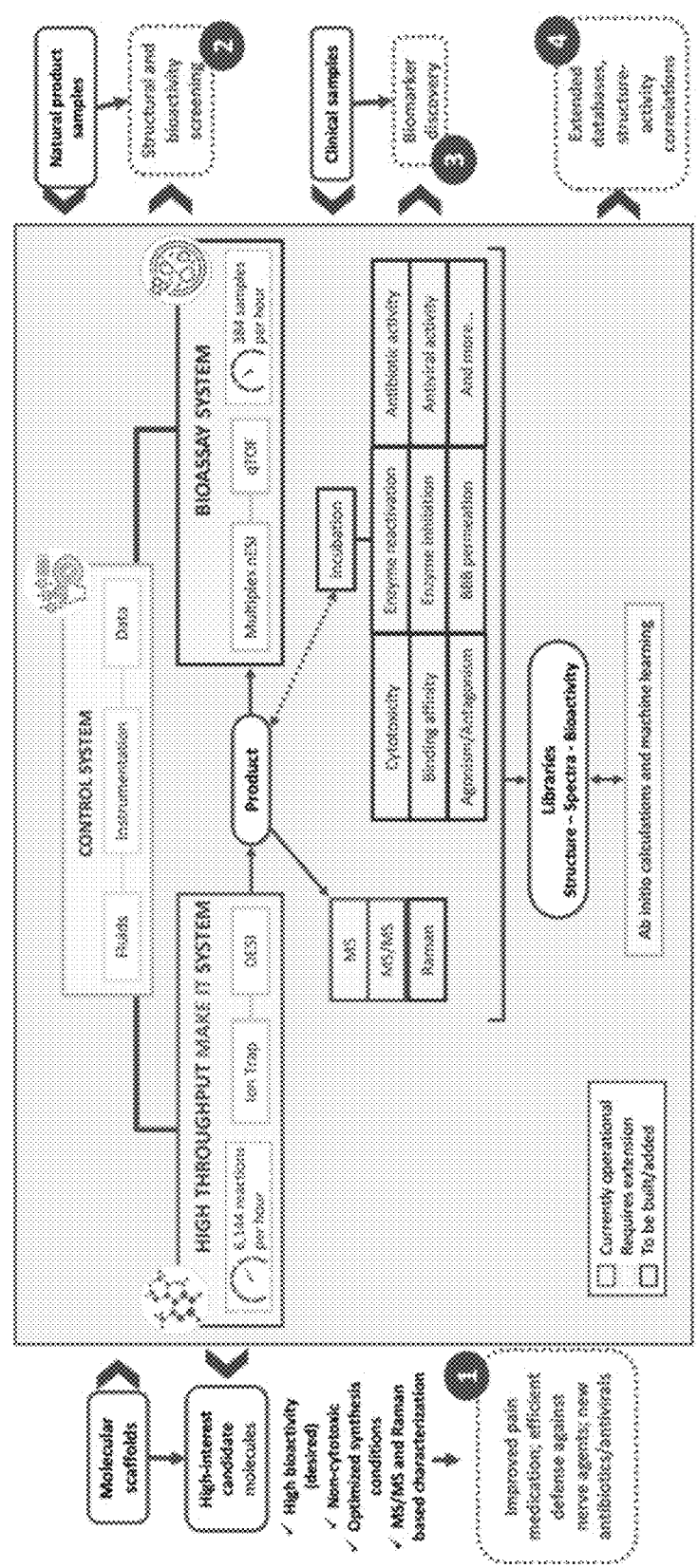
FIG. 2 describes another embodiment of the high-throughput platform.
Figure 3A:
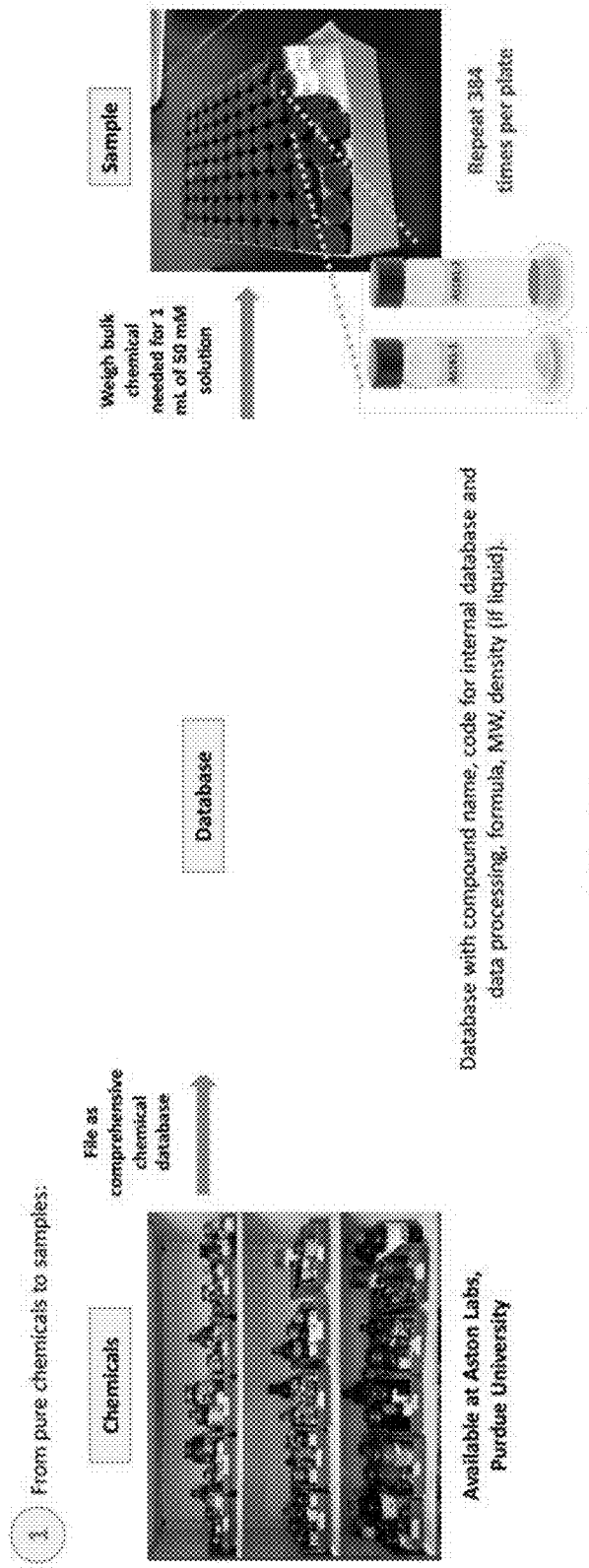
FIGS. 3A-D describe an exemplary work-flow using an embodiment of the high-throughput platform.
Figure 3B:
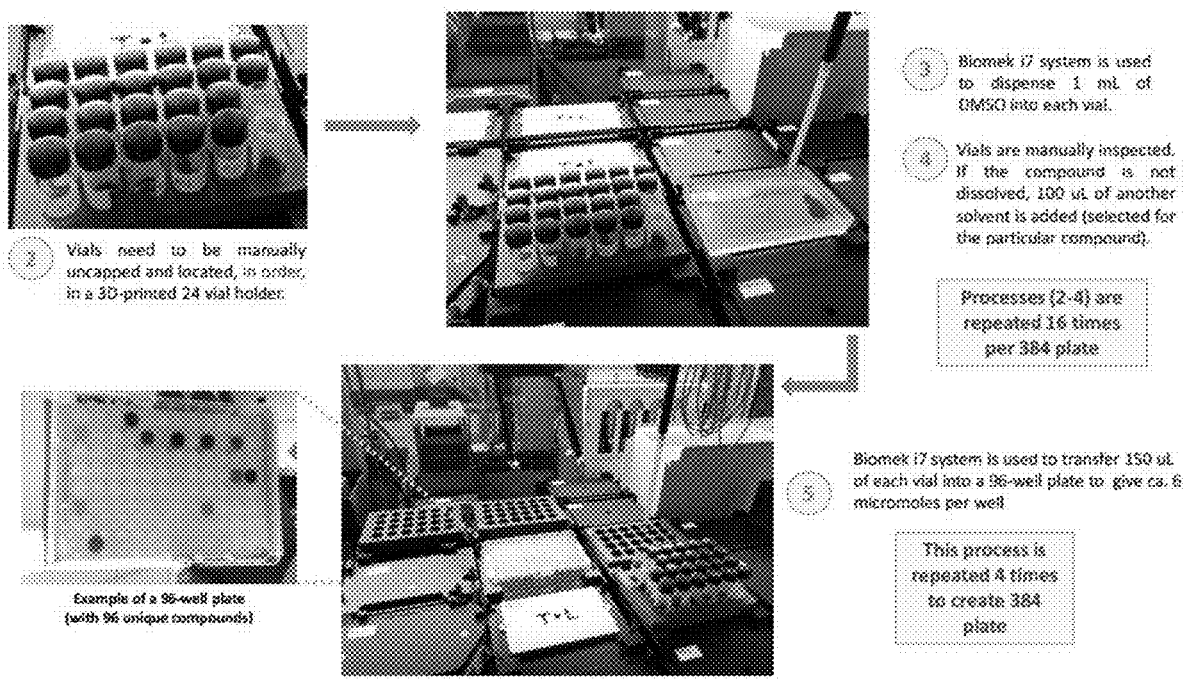
Figure 3C:
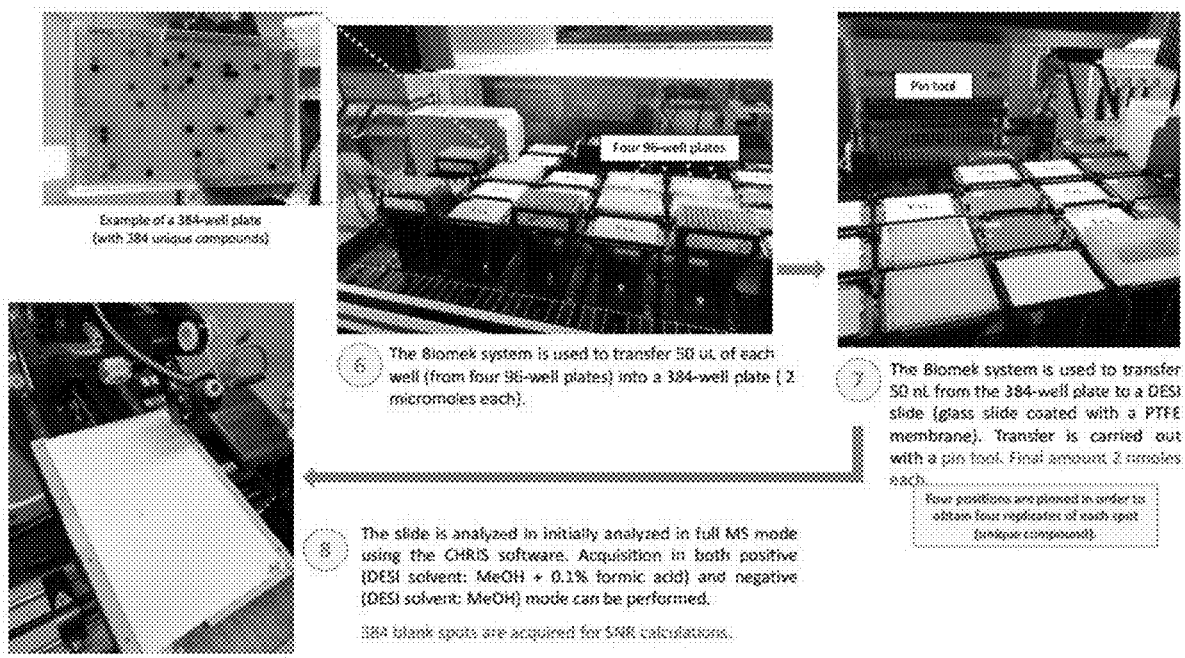
Figure 3D:
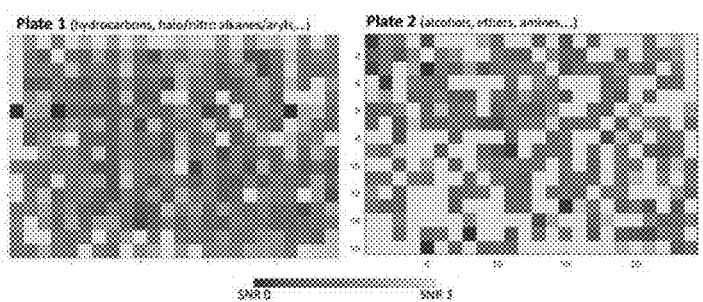
Figure 3D:
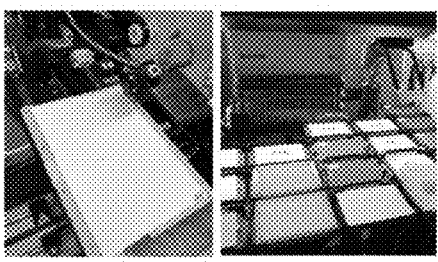

The invention generally relates to high-throughput label-free enzymatic bioassays using desorption electrospray ionization—mass spectrometry (DESI-MS). FIG. 1 describes an overview of the high-throughput platform. The fluid handling system controls sample handling and generates microwell plates of various sizes, exemplified here as a 384 well plate. The fluid handling system using a pinning device that interacts with the microwell plate to generate a substrate of discrete spots, using for example the pinning device. A DESI source is integrated as part of the system and directs a DESI active spray discharge onto each of the spots sequentially. The spray discharge desorbs and ionizes analytes from each spot, which are directed into a mass spectrometer for analysis. This high-throughput system has the capability of screening reaction products of interest at 1 second per reaction (or less) and is a system capable of 24-hour continuous operation. FIG. 2 describes another embodiment of the high-throughput platform with certain additional features. FIGS. 3A-D describe an exemplary work-flow using an embodiment of the high-throughput platform.

DESI is an ambient ionization method that allows the direct ionization of species from a sample, and is described in each of Takats et al., Science, 306:471-473, 2004 and Takats, U.S. Pat. No. 7,335,897, the content of each of which is incorporated by reference herein in its entirety. DESI-MS imaging is described for example in Eberlin et al. (Biochimica Et Biophysica Acta 2011, 1811(11):946-960) and Cooks R G, et al. (Faraday Discussions 2011, 149:247-267), the content of each of which is incorporated by reference herein in its entirety.

As mentioned above, this platform has broad applicability to many different chemical and biological systems. For example, the set of capabilities includes the ability, based on the measured mass spectra, to (i) read the contents of a microarray at high speed using DESI and to capture this information and process it automatically, (ii) reread the contents of a microarray at high speed using DESI after subjecting the samples in the array to exposure to chemical reagents or biological agents, (iii) use DESI to react mixtures of compounds present in the microarray, and simultaneously, record mass spectra of the secondary DESI droplets to characterize the reaction products, (iv) use DESI with added reagent in the spray (reactive DESI) to react (derivatize) compounds in the array and simultaneously to record mass spectra of the secondary droplets to characterize the derivatized compounds, and (v) use DESI to characterize biomarkers and other features of tissue in array format. In some cases, the DESI analysis conditions might be chosen to minimize the possibility of accelerated reaction in a secondary microdroplets. In some cases, the sample to MS inlet and other analysis parameters might be chosen to maximize the possibility of such accelerated reactions occurring.

The information obtained from reading the contents of a microarray at high speed using DESI allows for (i) optimization of synthesis conditions for maximum yields and/or product purities when the reactions studied are scaled up using flow chemistry or conventional bulk synthesis, (ii) systematic studies of reaction mechanisms over a range of conditions by characterization of reaction intermediates as an additional route to information that will facilitate reactions on any scale, (iii) collection of small amounts of synthetic product from the droplet reactions on a receiver surface, (iii) measurement of the cytotoxicity of the small amounts of material collected by fluorescence measurements as is well known in the state of the art, (iv) characterization of the purity of the collected product by independent MS and/or MS/MS measurements, (v) compilation of the optical and MS/MS spectra on the small amounts of collected new compounds in a database for forensic and other uses, (vi) measurement of binding assays by label free MS after exposing the collected product to an enzyme or receptor or other substrate, and (vii) determination of structure/activity relationships using bioactivity measurements on collected products. Certain embodiments focus on measurement of binding assays by label free MS after exposing the collected product to an enzyme or receptor or other substrate.

Figure 4:
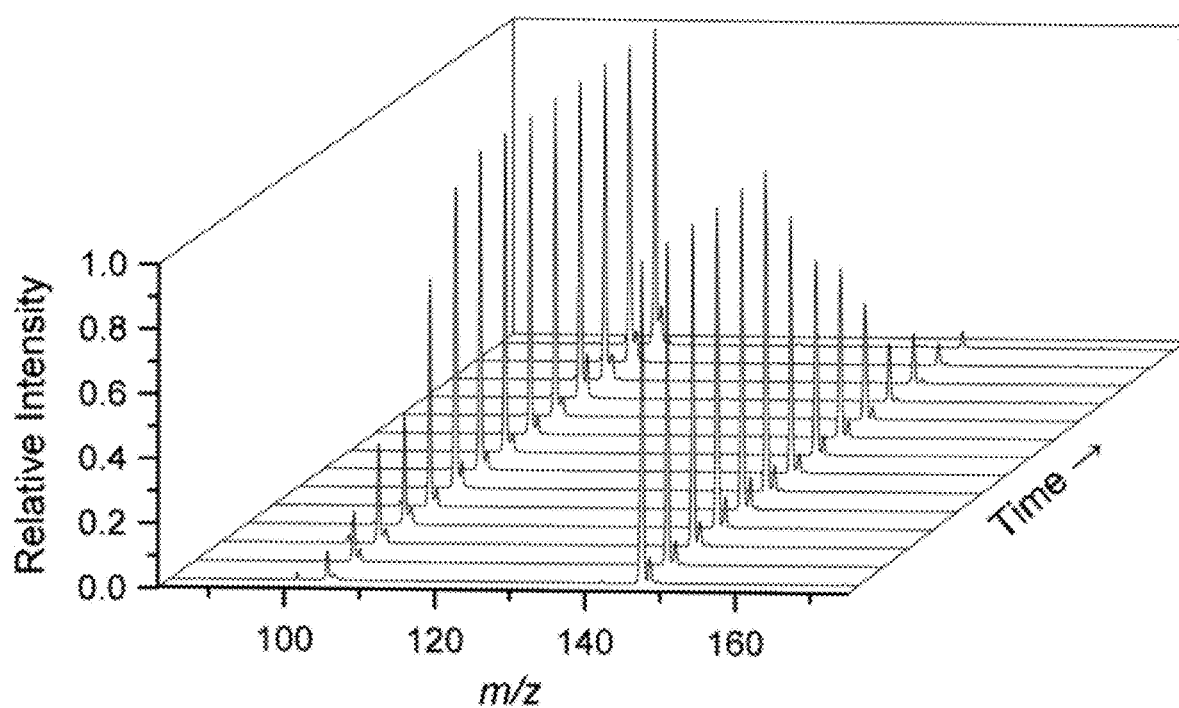
FIG. 4. is a graph showing representative examples of the spectra obtained for the monitoring of enzymatic reactions using the platform described herein directly from the bioassay mixture containing both surfactants and non-volatile buffers.

The platform described herein was used to perform enzymatic bioassays in a high-throughput and label-free manner (FIG. 4). Initial efforts were focused on studying the acetylcholinesterase (AChE) assay, which is relevant in the context of drug discovery for Alzheimer's disease as well as the development of contra-measures against chemical warfare agents. To develop the bioassays the substrate (acetylcholine, m/z 146) and product (choline, m/z 104) of the enzymatic reaction were simultaneously monitored. The analysis was performed using DESI-MS (spray solvent: MeOH-ACN 1:1) directly from the bioassay mixture (enzyme, phosphate buffer 0.1 M pH 8, 0.1% BSA) after quenching with ACN (up to 50% final concentration) and pinning (50 nL) on PTFE-coated glass slides. The effective analysis time per sample (spot) is as little as 0.3 seconds, in such a way that a 384-sample array can be analyzed completely in 7 minutes. Kinetic studies are readily performed by quenching aliquots after fixed time intervals (typically 1-2 minutes). The figure illustrates the quality of the spectra obtained over the m/z range of interest, as well as the behavior of the product and substrate throughout the reaction. The reaction time to completion can be optimized by selecting appropriate amounts of enzyme and substrate, depending on the objective of the study.

Figure 5:
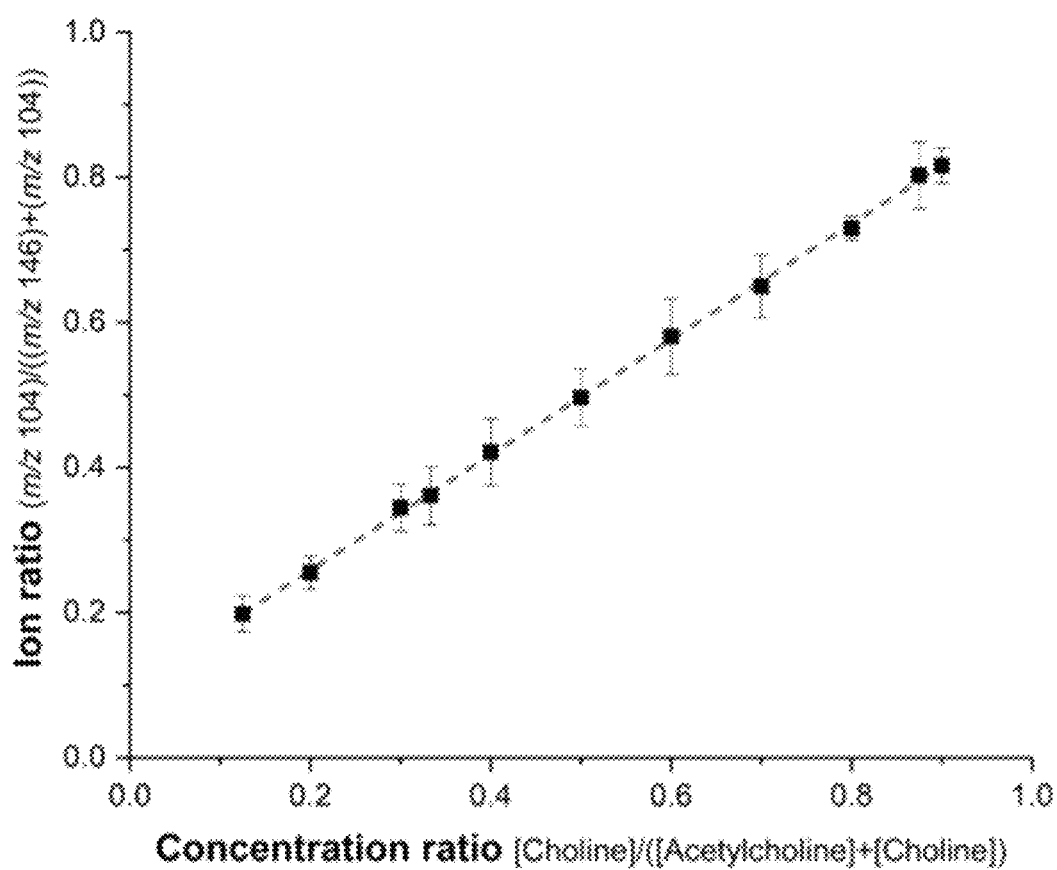
FIG. 5 shows that empirical progress of the reaction calculated from the DESI-MS data (using intensities of the ions (m/z 104)/(m/z 146+m/z 104)) can be directly converted into actual reaction progress ([choline]/([acetylcholine]+[choline]) using a simple calibration curve between the measured ion ratios and the actual concentration ratios of choline and acetylcholine in the mixture.

FIG. 5 shows that empirical progress of the reaction calculated from the DESI-MS data (using intensities of the ions (m/z 104)/(m/z 146+m/z 104)) can be directly converted into actual reaction progress ([choline]/([acetylcholine]+[choline]) using a simple calibration curve between the measure ion ratios and the actual concentration ratios of choline and acetylcholine in the mixture. The calibration curve shown here was built using 6 independent solutions of different total concentrations (range: 0.4-1.0 mM), that underwent the same procedure as did the bioassay samples (ACN addition and pinning). Note that the amount of material used for the analysis is on the order of 100-300 pg. Each data point represents the average of the six solutions, each analyzed four times on three different days, for a total of 72 measurements per concentration ratio. The acquisition time for this daily calibration (246 spots) is around 5 minutes. This calibration allows direct determination of kinetic parameters of the enzymatic reaction without the need for labeled compounds (either deuterated standards or non-native substrates).

Figure 6:
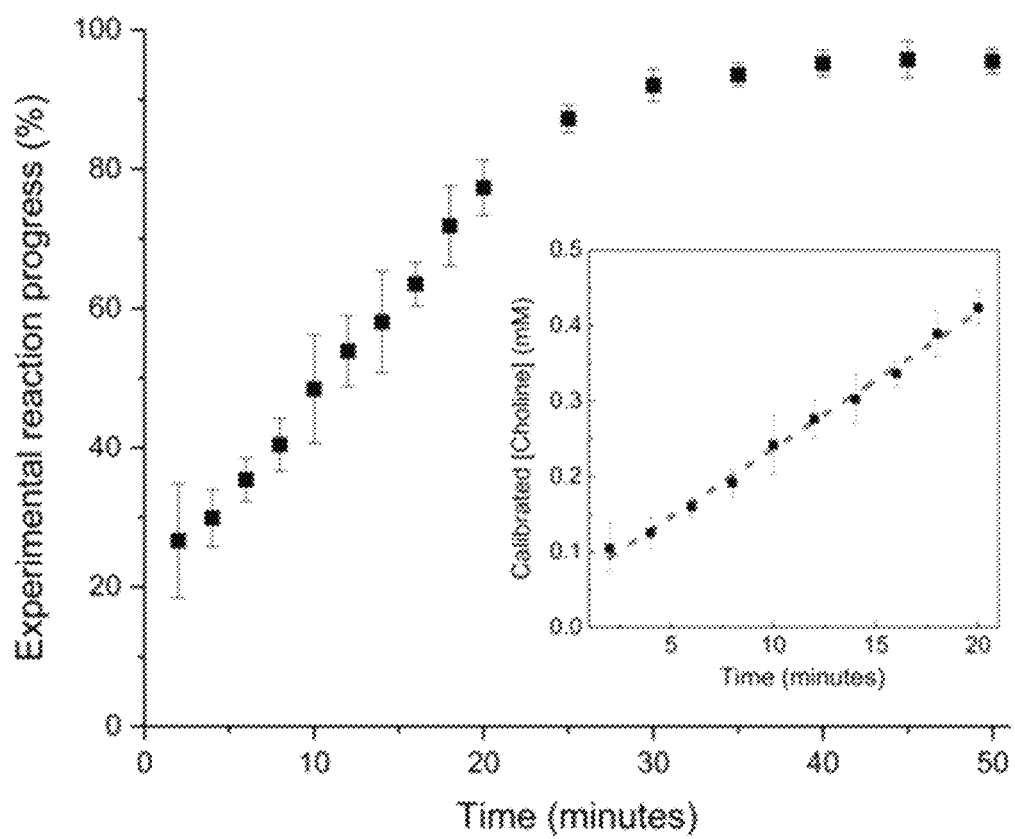
FIG. 6 shows that progress of the enzymatic reaction can be readily obtained by quenching aliquots of the bioassay mixture every 1-5 minutes and measuring choline ion ratio (using intensities of the ions (m/z 104)/(m/z 146+m/z 104)) vs. time.

FIG. 6 shows progress of the enzymatic reaction can be readily obtained by quenching aliquots of the bioassay mixture every 1-5 minutes and measuring choline ion ratio relative to acetylcholine+choline vs. time. For kinetic determinations the reactions were incubated for 50 minutes, with the concentration of substrate held kept between 0.4 to 1 mM, while the concentration of enzyme was set to 180 ng/mL. The linear section of the curve was converted to choline concentration, using the calibration curve shown in FIG. 5. Note that only concentrations within the calibration range were used. The calibrated result (inset) is used to determine $v0$ of the reaction. The data shown come from eight instrumental replicates from a single mixture (128 spots), acquired in less than 2.5 minutes.

Figure 7:
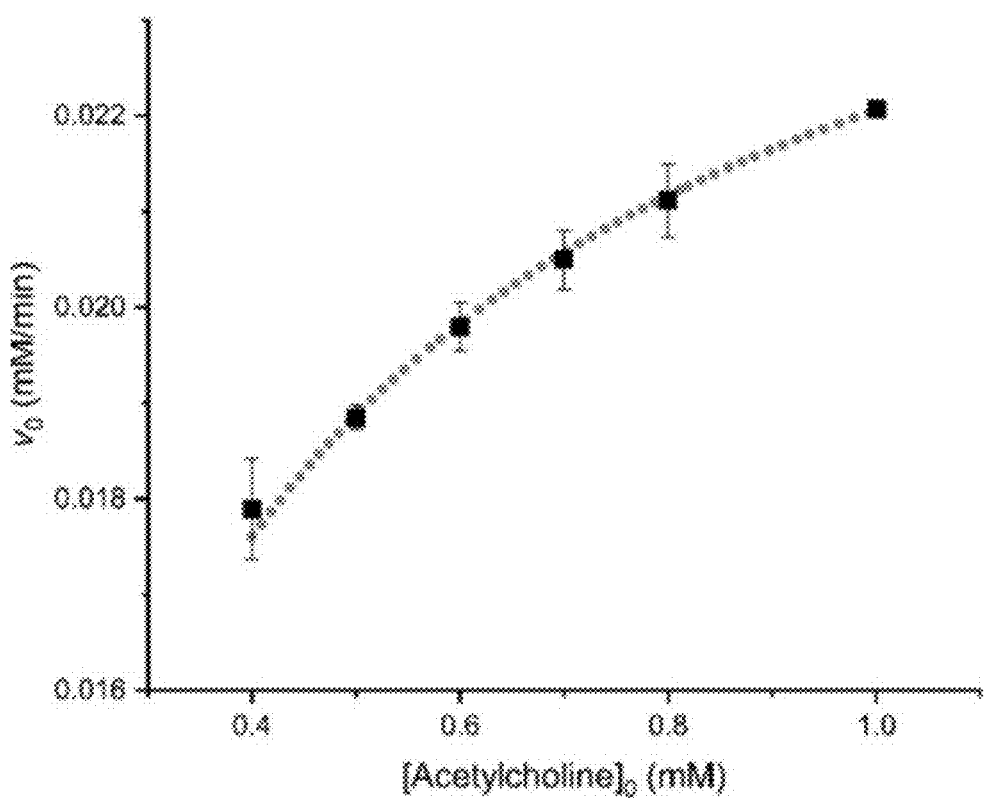
FIG. 7 shows that the Michaelis-Menten plot for acetylcholinesterase (AChE) was built using 18 independent reaction progress curves (independent triplicates of six substrate concentrations: 0.4, 0.5, 0.6, 0.7, 0.8, 1.0 mM).

FIG. 7 shows that the Michaelis-Menten plot for AChE was built using 18 independent reaction progress curves (independent triplicates of six substrate concentrations: 0.4, 0.5, 0.6, 0.7, 0.8, 1.0 mM). The curve was used to estimate the Michaelis-Menten constant of the system as $0.203\pm0.006$ mM, which is within the range of values reported in the literature (0.08 to 0.23 mM). Construction of this plot, by measuring eight instrumental replicates of each data point in each reaction progress curve, required the analysis of 2304 spots, which can be readily done in around 30 minutes. Note that the incubation (50 minutes) for all the samples can be performed simultaneously, so that only 80 minutes in total is required for the kinetic characterization of the reaction.

Figure 8:
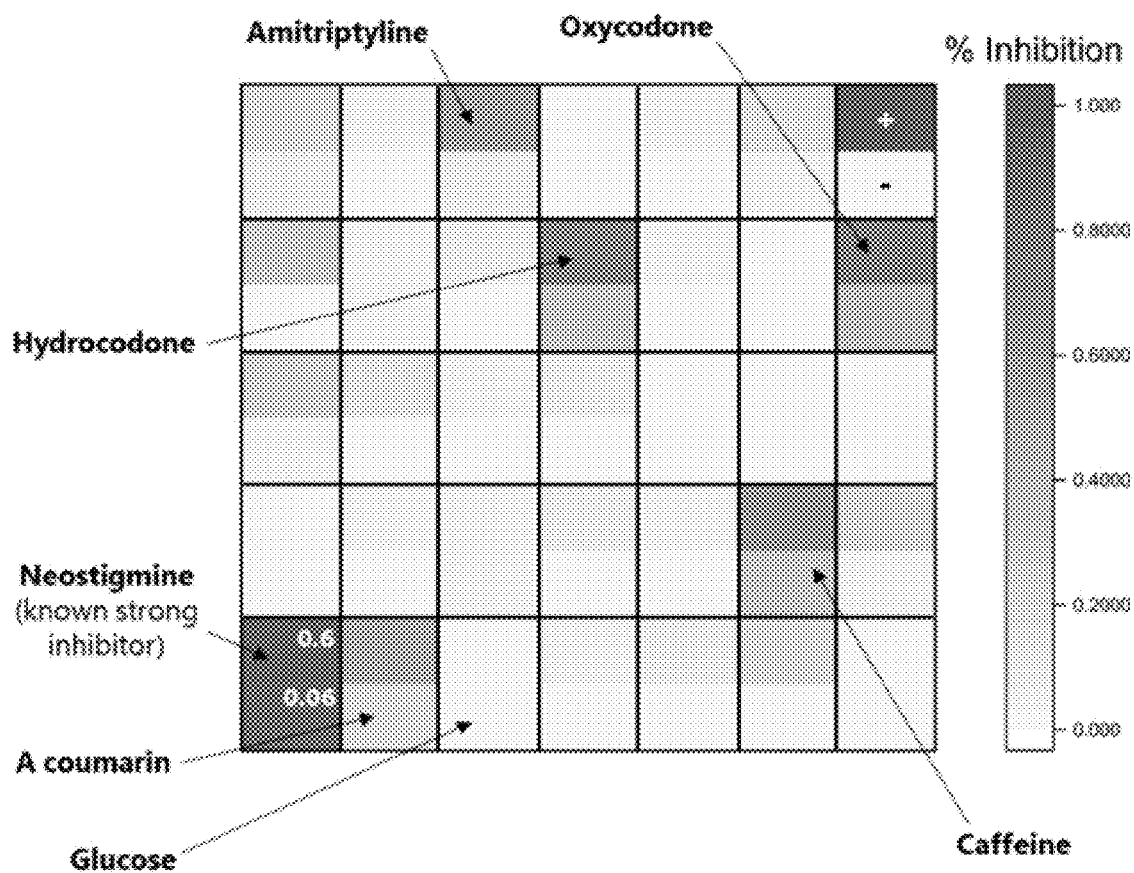
FIG. 8 shows that using higher concentrations of enzyme and substrate, 9 µg/mL and 5 mM, respectively, the reaction can be completed in five minutes and 384 inhibition reactions are analyzed in <15 min while excellent sensitivity is achieved.

FIG. 8 shows that using higher concentrations of enzyme and substrate, 9 µg/mL and 5 mM, respectively, the reaction can be completed in five minutes and excellent sensitivity is achieved. Under these conditions 34 compounds were tested as potential inhibitors of AChE: 1 known strong inhibitor (neostigmine), 17 natural products and 16 drugs of abuse. The compounds were tested at two different concentrations (high and low: 0.6 and 0.06 mM), and both positive and negative controls were analyzed in the same assay. All the samples were analyzed in quadruplicate (for a total of 280 spots), the whole set requiring less than 6 minutes of analysis time. Note that if no replicates are analyzed, 384 inhibitors can be all tested in less than 15 minutes total (5-minute incubation+7-minute analysis+2-minute data processing).

Figure 9:
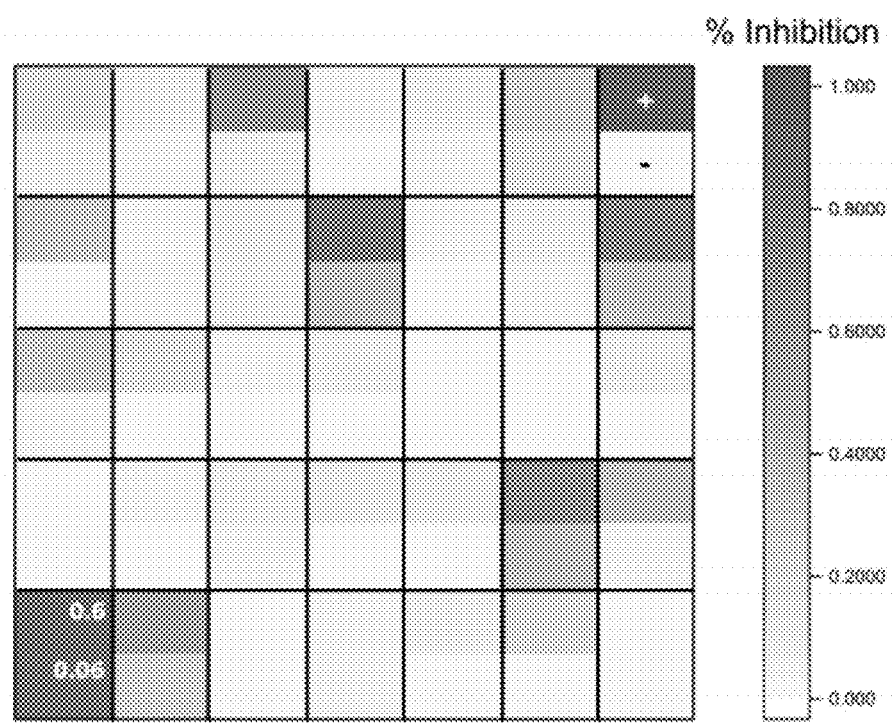
FIG. 9 shows that robustness of the approach was checked using a different DESI source and a different mass spectrometer (Waters source and Synapt G2 qToF).
Figure 10:
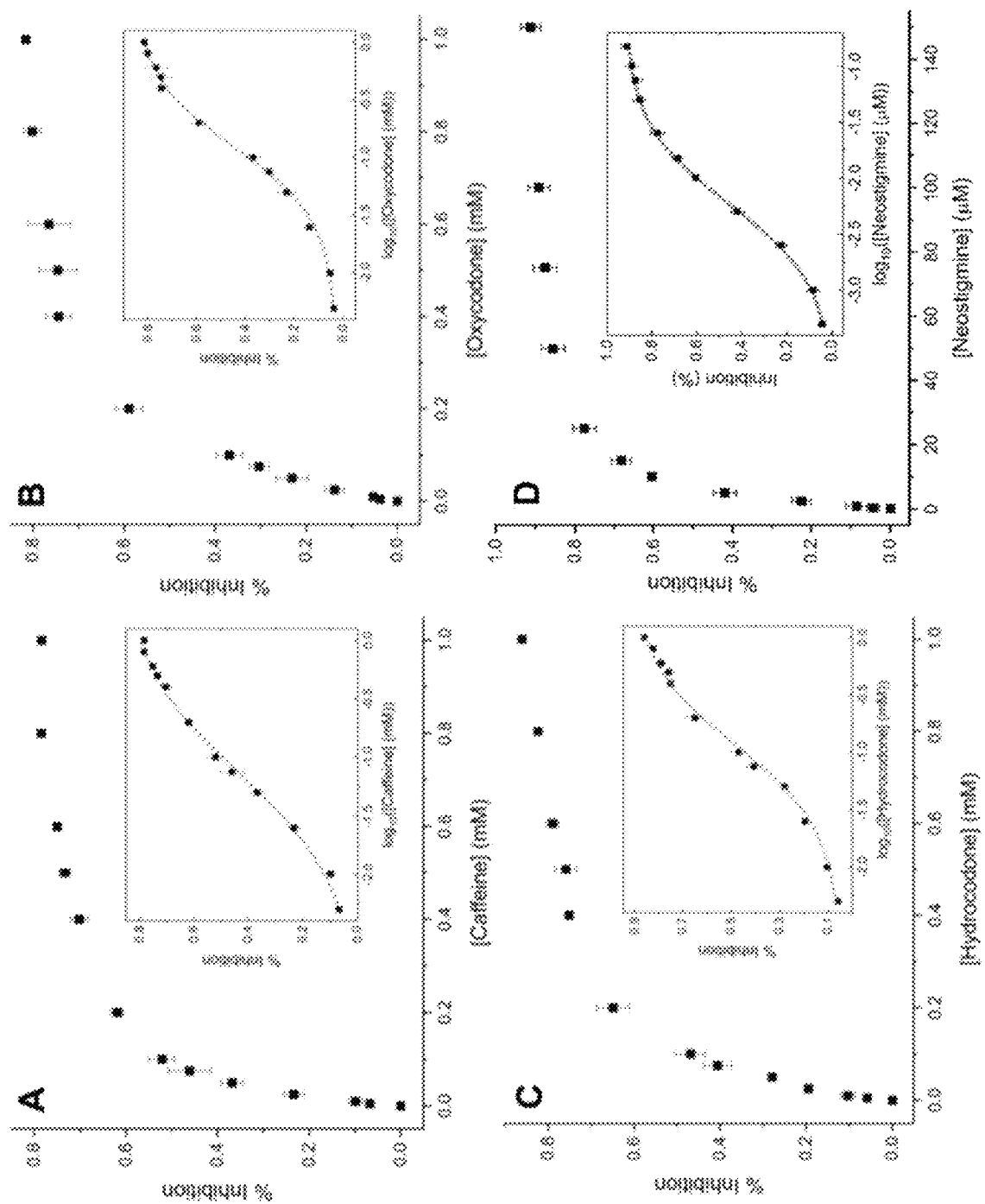
FIG. 10 panels A-D show that inhibitors of interest (i.e. which show relatively high activity compared to a known inhibitor in the initial high-low screening) can be then further studied.

Robustness of the approach was checked using a different DESI source and a different mass spectrometer (Waters source and Synapt G2 qToF) (FIG. 9). Results for the inhibition assays are almost identical to those shown in the heatmap of FIG. 8 (Prosolia source and Thermo LTQ ion trap).

Inhibitors of interest (i.e. which show relatively high activity compared to a known inhibitor in the initial high-low screening) can be then further studied (FIGS. 10A-D). From the original set of 34 compounds screened four—neostigmine, oxycodone, hydrocodone and caffeine—were selected and dose-response curves were obtained for all of them. With these curves the IC50 values of these compounds under our particular assay conditions were found as 5.9, 0.122, 116 and 71 µM for neostigmine, oxycodone, hydrocodone and caffeine, respectively, which agrees with the expected trend. Each of these dose-response curves represents the average of three independent solutions with eight instrumental replicates each. In total, 1536 reactions were analyzed to obtain the four curves presented here, the total analysis requiring around 25 minutes.

Figure 11:
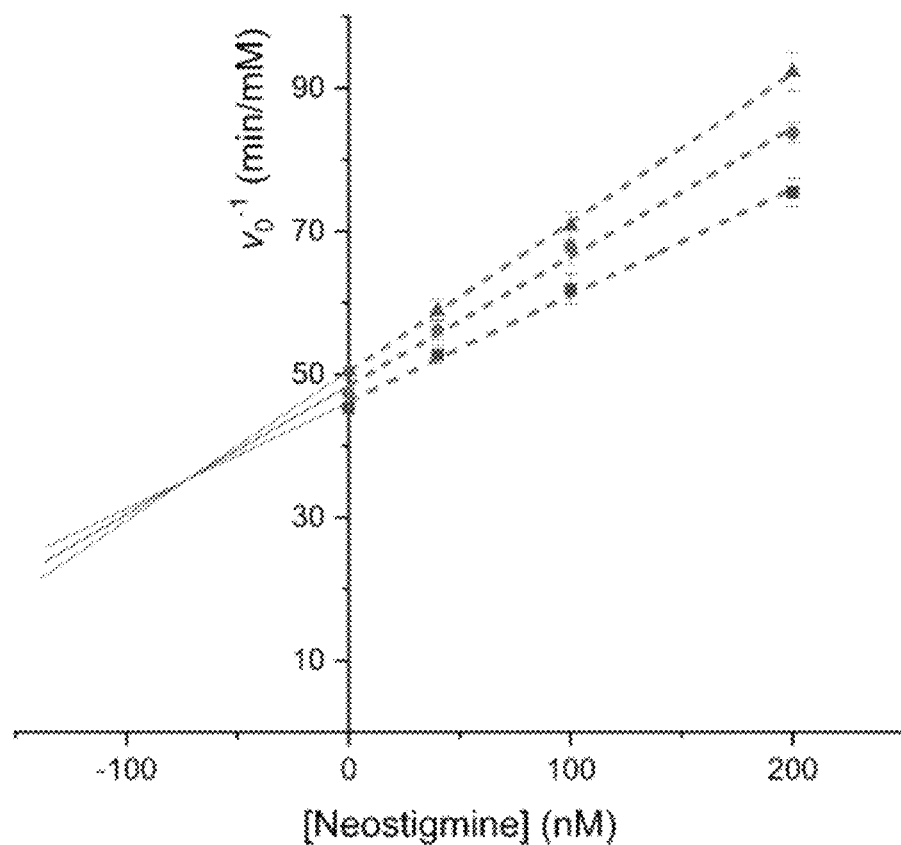
FIG. 11 shows that further characterization of the inhibitors was achieved by screening simultaneously different concentrations of inhibitor and the substrate in order to obtain the Dixon plot from which the inhibition constant was rapidly determined as 70.0±0.7 nM.

Further characterization of the inhibitors was achieved by screening simultaneously different concentrations of inhibitor and the substrate in order to obtain the Dixon plot (FIG. 11). Neostigmine was chosen for this further characterization. This Dixon plot required that 24 independent progress curves be determined: duplicate measurements taken on 12 combinations of concentrations of inhibitor (0, 40, 100, 200 nM) and substrate (0.6, 0.8, 1.0 mM). This required the analysis of 3072 spots, carried out in approx. 35 minutes, with simultaneous incubation time of 50 minutes. As expected, the position of the intersection of the lines in the plot indicates that neostigmine is a competitive inhibitor. Its inhibition constant was determined as 70.0±0.7 nM, a value comparable to those reported for this enzyme-inhibitor complex.

Figure 12:
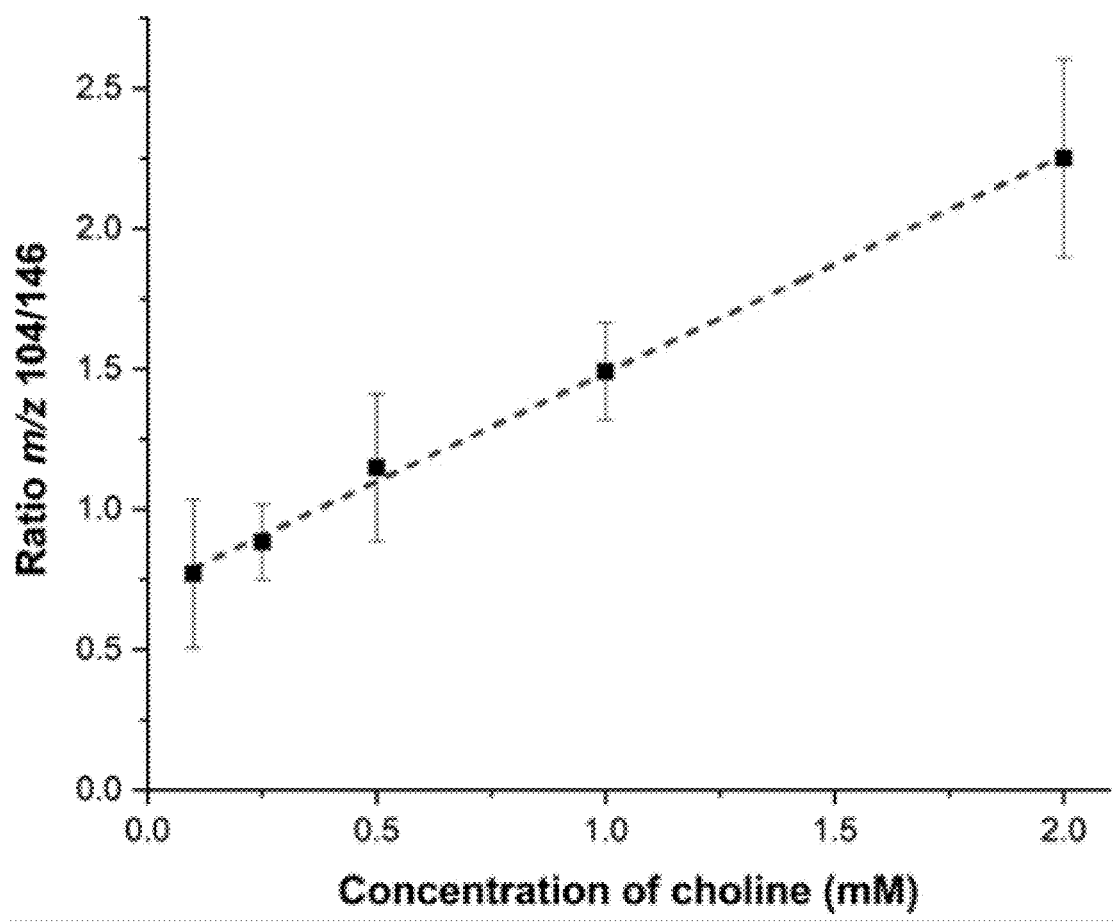
FIG. 12 panels A-C show that acetylcholinesterase reactivators can be screened against different inhibitors of interest, characterizing the dynamics of both inhibition and reactivation.

FIG. 12 shows that the dynamics of enzymatic inhibition-reactivation processes can be studied. The figure shows the inhibition of acetylcholinesterase throughout its incubation with 5 dichlorovos (panel A), 0.25 µM chlorpyrifos-oxon (panel B), and 0.75 µM paraoxon (panel C), as well as the enzyme reactivation due to the addition of a commercial reactivator (2-pralidoxime, 100 µM). Addition of the oxime reactivator is indicated by the solid gray line in the plots. Reactivation efficiencies of 45±2%, 87±5% and 76±3% were observed after inhibition with dichlorovos, chlorpyrifos-oxon, and paraoxon, respectively.

System Architecture

In certain embodiments, the systems and methods of the invention can be carried out using automated systems and computing devices. Specifically, aspects of the invention described herein can be performed using any type of computing device, such as a computer, that includes a processor, e.g., a central processing unit, or any combination of computing devices where each device performs at least part of the process or method. In some embodiments, systems and methods described herein may be controlled using a handheld device, e.g., a smart tablet, or a smart phone, or a specialty device produced for the system.

Systems and methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. For example, the reference set of data may be stored at a remote location and the computer communicates across a network to access the reference set to compare data derived from the female subject to the reference set. In other embodiments, however, the reference set is stored locally within the computer and the computer accesses the reference set within the CPU to compare subject data to the reference set. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 16:
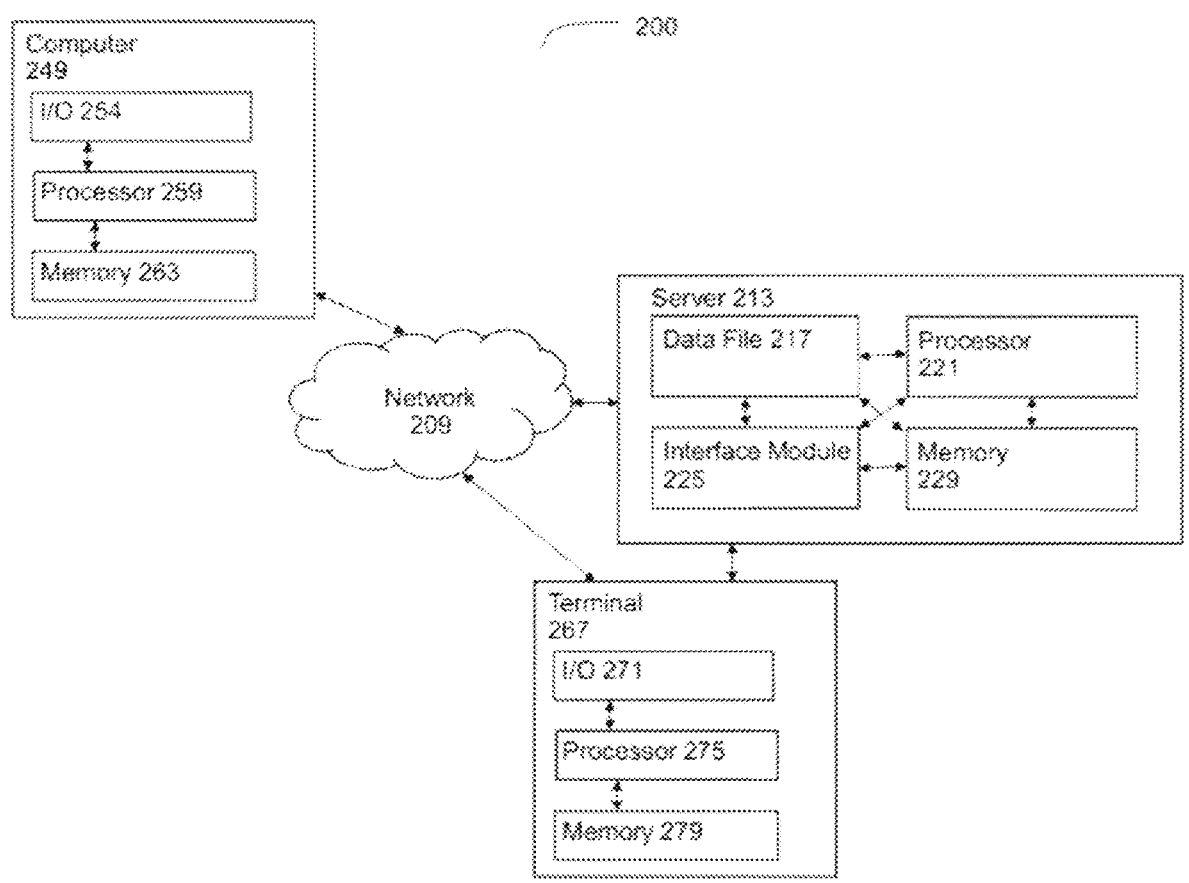
FIG. 16 is an illustration showing an exemplary data analysis module for implementing the systems and methods of the invention in certain embodiments.

In an exemplary embodiment shown in FIG. 16, system 200 can include a computer 249 (e.g., laptop, desktop, or tablet). The computer 249 may be configured to communicate across a network 209. Computer 249 includes one or more processor 259 and memory 263 as well as an input/output mechanism 254. Where methods of the invention employ a client/server architecture, steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

Multiplexing and Inductive Charging

In certain embodiments, multiplexing on sample loading and analysis is used in the systems and methods of the invention, optionally using inductive charging for analysis. Such approaches are described for example in U.S. patent application publication number 2020/0381238, the content of which is incorporated by reference herein in its entirety. In certain embodiments, the induced DC nESI ionization source includes a 3D electrical controlled moving platform, emitter holder and a pogo pin holder. In such embodiments, the emitter holder is preloaded with 96 emitters and samples. The emitter holder is attached to the 3D moving stage by a 3D printed connector. The emitter holder is designed to easily attached and detached from the moving stage for convenience of sample introduction and cleaning. The front (side facing the MS inlet) of the emitter holder has 96 holes to hold 96 emitters. Inside the holes, there are 96 individual electrodes with the same length as the emitter holder. When loading the emitters into the holder, these electrodes are inserted into the emitters but do not reach the sample solution. The other ends of the electrodes go from the rear (side opposite from the MS inlet) and are soldered to a PCB with 96 holes. On the PCB, there are 96 isolated copper layers electrically in contact with the 96 electrodes by soldering. A pogo pin electrode placed behind the PCB is aligned with the MS inlet. The position of the pogo pin electrode is fixed by the pogo pin holder on a fixed arm of the 3D moving stage. The pogo pin electrode touches the PCB. When the device is running, the motion control system first goes to the top right starting point and moves in the vertical y-direction to find the first row of emitters and then moves in the horizontal x-direction to analyze samples in the first row in sequence. When an emitter is aligned with the MS inlet, the pogo pin touches the corresponding copper layer on the PCB and 2-3.5 kV volts is applied to the electrode for induced DC nESI ionization of the sample in the tip of the emitter. Note that the electrode does not contact the sample so ionization is induced. Because the flow rate in inductive nESI is very low, so there is enough time to record the high-quality MS data in spite of very small sample volume.

To solve the problem of sample introduction presented by the traditional nESI work flow, we have developed a "dip and go" strategy using a multiplexed system. In such an approach, 96 emitters with 20-micron tip size are preloaded into the emitter holder. The size of the holder is designed to correspond to the size of the standard 96-well plate and the position of each emitter corresponds to the position of each well in the 96-well plate. To load the sample, one holds the emitter holder and lets the side with emitters face the 96-well plate, lowers the holder and allows every emitter to be immersed into sample solution for 10 seconds and then lifts the holder. This procedure can be done manually or with a robot. The amount of sample solution introduced into emitter is ca. 100 nL. Sample loading amounts can be varied by using different loading times.

Induced electrophoretic cleaning ("desalting") can be applied to the samples on the emitters prior to sample analysis to achieve better analytical performance for samples with a complex matrix. By applying voltage (e.g., more than 5 kV, with either the same or opposite polarity to that used for nESI analysis) to the electrodes simultaneously, the high electrical field induced in the sample in the emitter tip will cause electrophoresis. Ions with large ionic mobility such as anions and cations from simple salts in the solution will migrate towards the two ends of the solution, leaving substances with small ionic mobility such as peptides will remain essentially in their original positions and will be subject to selective ionization.

To perform offline electrophoretic cleaning one holds the emitter holder and allows the copper layer of the PCB touch a copper plate connected to the high voltage output of a power supply. At 0.5 to 1 cm distance from the emitter tip, another copper plate which is grounded is placed so as to set up a large potential change in the sample solution to initiate electrophoresis. The electrophoresis is maintained for 10 seconds and then the emitter holder is re-installed onto the back to the 3D moving stage platform. Following the same steps described in section A one records spectra of the cleaned samples. This method is more convenient but slightly slower (because cleaning slightly slows the rate of motion used for ionization).

The alternative to offline cleaning is to perform online cleaning using one HV supply for cleaning and a second one for ionization. To perform online electrophoretic cleaning, the emitter holder is attached to the moving stage. When performing the cleaning, the moving stage allows the emitter holder to move from left to right. The left pogo pin on a pogo pin holder is supplied with −6 kV volts to induce electrophoretic cleaning of the sample that points towards the grounded counter electrode. Subsequently, after cleaning, the emitter moves and is aligned with the MS inlet at which point the right pogo pin electrode with 2 to 3.5 kV volts applied to the pogo pin holder initiates inductive nESI analysis of sample in the emitter by the same process described in A. This method is faster and the sample screening rate can be maximized.

As mentioned above, inductive charging can be useful in a multiplex analysis setting. Inductive charging is further described for example in U.S. Pat. No. 9,184,036, the content of which is incorporated by reference herein in its entirety. In inductive charging the probe includes a spray emitter and a voltage source and the probe is configured such that the voltage source is not in contact with the spray emitter or the spray emitted by the spray emitter. In this manner, the ions are generated by inductive charging, i.e., an inductive method is used to charge the primary microdroplets. This allows droplet creation to be synchronized with the opening of the sample introduction system (and also with the pulsing of the nebulizing gas). Inductive nESI can be implemented for various kinds of nESI arrays due to the lack of physical contact. Examples include circular and linear modes. In an exemplary rotating array, an electrode placed mm from each of the spray emitters in turn is supplied with a 2-4 kV positive pulse (10-3000 Hz) giving a sequence of ion signals. Simultaneous or sequential ions signals can be generated in the linear array using voltages generated inductively in adjacent nESI emitters. Nanoelectrospray spray plumes can be observed and analytes are detected in the mass spectrum, in both positive and negative detection modes. In the electrophoretic clean-up working mode, direct current voltage source (1.5-6 kV) was used to induce nanoelectrospray. Different from the previous example induced by alternating current voltage, the induced electrical field keeps the same direction in this mode, which ensures efficient electrophoretic cleaning performance.

Ion Traps and Mass Spectrometers

Any ion trap known in the art can be used in systems of the invention. Exemplary ion traps include a hyperbolic ion trap (e.g., U.S. Pat. No. 5,644,131, the content of which is incorporated by reference herein in its entirety), a cylindrical ion trap (e.g., Bonner et al., International Journal of Mass Spectrometry and Ion Physics, 24(3):255-269, 1977, the content of which is incorporated by reference herein in its entirety), a linear ion trap (Hagar, Rapid Communications in Mass Spectrometry, 16(6):512-526, 2002, the content of which is incorporated by reference herein in its entirety), and a rectilinear ion trap (U.S. Pat. No. 6,838,666, the content of which is incorporated by reference herein in its entirety).

Any mass spectrometer (e.g., bench-top mass spectrometer of miniature mass spectrometer) may be used in systems of the invention and in certain embodiments the mass spectrometer is a miniature mass spectrometer. An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), and Sokol et al. (Int. J. Mass Spectrom., 2011, 306, 187-195), the content of each of which is incorporated herein by reference in its entirety.

The control system of the Mini 12 (Linfan Li, Tsung-Chi Chen, Yue Ren, Paul I. Hendricks, R. Graham Cooks and Zheng Ouyang "Miniature Ambient Mass Analysis System" Anal. Chem. 2014, 86 2909-2916, DOI: 10.1021/ac403766c; and 860. Paul I. Hendricks, Jon K. Dalgleish, Jacob T. Shelley, Matthew A. Kirleis, Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 9. It may have a size similar to that of a shoebox (H20 cm×W25 cm×D35 cm). In certain embodiments, the miniature mass spectrometer uses a dual LIT configuration, which is described for example in Owen et al. (U.S. patent application Ser. No. 14/345,672), and Ouyang et al. (U.S. patent application Ser. No. 61/865,377), the content of each of which is incorporated by reference herein in its entirety.

EXAMPLES

Example 1

A calibration curve of choline (m/z 104) was obtained by the high throughput approach and using acetylcholine (0.25 mM, m/z 146) as internal standard (FIG. 12). All samples were prepared in the bioassay matrix (0.1 M phosphate buffer, pH 8, 0.1% BSA) and analyzed without any pretreatment. Nine individual samples were prepared at each concentration (and blank) using the fluidic handling robot, and then pinned four times as 50 nL spots in different locations on the same PTFE-coated plate, giving a total of 216 spots. DESI-MS was used for the analysis of the plate in positive ion mode (spray solvent: MeOH, applied voltage: 4 kV, instrument: ion trap). Data acquisition and processing was controlled by the CHRIS software. The effective analysis time of all the spots was under four minutes. Each data point in the calibration curve represents the average of 36 spots (9 individual solutions, 4 replicates each). The coefficient of determination (R2) of the linear model adjusted to fit the data is 0.998. Results are reproducible after pinning different slides on different days.

Example 2

Figure 13:
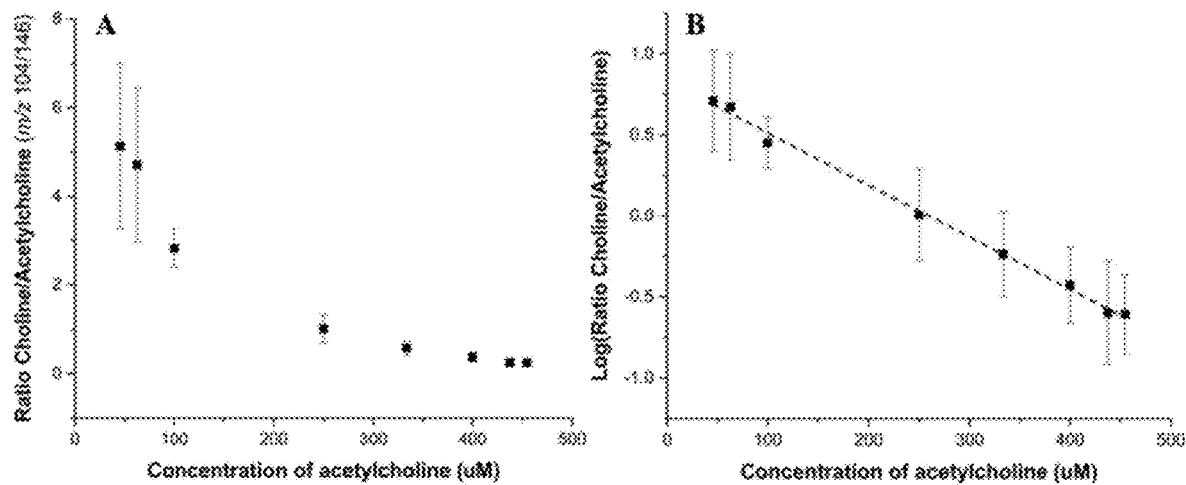
FIG. 13 panel A shows a simulated inhibition plot used to assess the performance of the approach.

FIG. 13 panel A shows a simulated inhibition plot used to assess the performance of the approach. Eight different ratios of choline/acetylcholine (m/z 104/146) were explored, keeping constant the total concentration of substrate plus product ([choline]+[acetylcholine]=500 μM). These solutions simulated the results from an inhibition experiment (in which the transformation of acetylcholine to choline would reduce the acetylcholine ratio as the concentration of inhibitor increases). The expected behavior (over at least a region of the curve) is logarithmic. As observed FIG. 13 panel B, the log-transformed data shows the expected linear behavior (R2=0.996). This demonstrates how our approach could be used to calculate IC50 values without the need for internal standards, labels or sample pretreatment. All solutions were prepared in the bioassay matrix (0.1 M phosphate buffer, pH 8, 0.1% BSA) using the fluidic handling robot and then rapidly pinned four times on the same PTFE-coated plate. DESI-MS was used for the analysis of the plate in positive ion mode (spray solvent: MeOH, applied voltage: 4 kV, instrument: Thermo linear ion trap). Data acquisition and processing was controlled by the CHRIS software. In both plots each data point represents the average of 12 spots (3 independent solutions, 4 replicates each). The effective analysis time of all the spots (including blanks) was under 3 minutes.

Example 3

Figure 14:
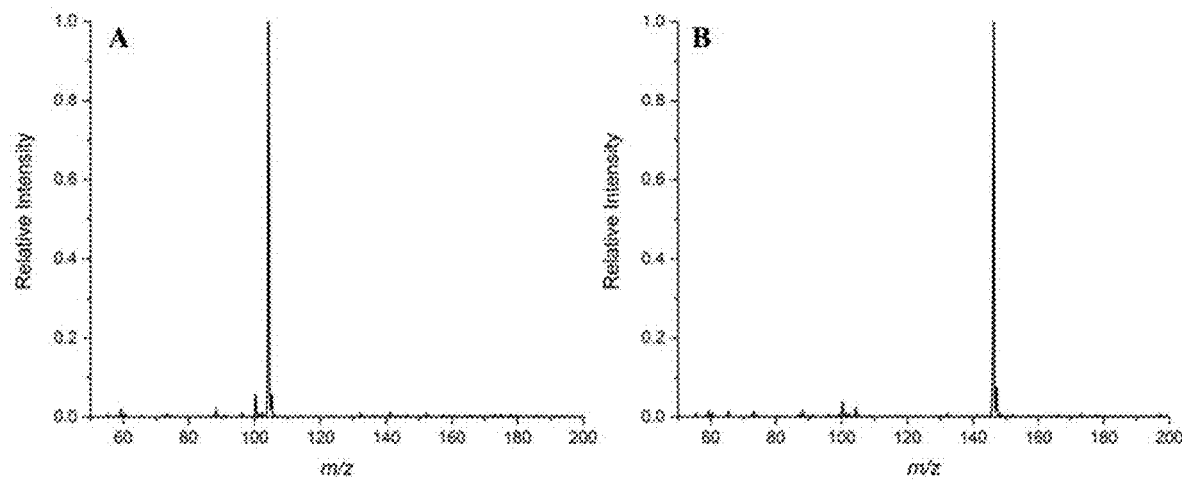
FIG. 14 panels A-B show representative mass spectra of a bioassay mixture (panel A) just after enzyme addition and (panel B) after 30 minutes of room temperature incubation (in 0.1 M phosphate buffer, pH 8, 0.1% BSA).

FIG. 14 panels A-B show representative mass spectra of a bioassay mixture (panel A) just after enzyme addition and (panel B) after 30 minutes of room temperature incubation (in 0.1 M phosphate buffer, pH 8, 0.1% BSA). As it can be observed, acetylcholine (m/z 146) was completely transformed to choline (m/z 104) after incubation under the experimental conditions. Data were acquired using DESI-MS in positive ion mode (spray solvent: MeOH, applied voltage: 4 kV, instrument: ion trap) without any sample pretreatment, just after spotting of the bioassay mixture.

Example 4

Figure 15A:
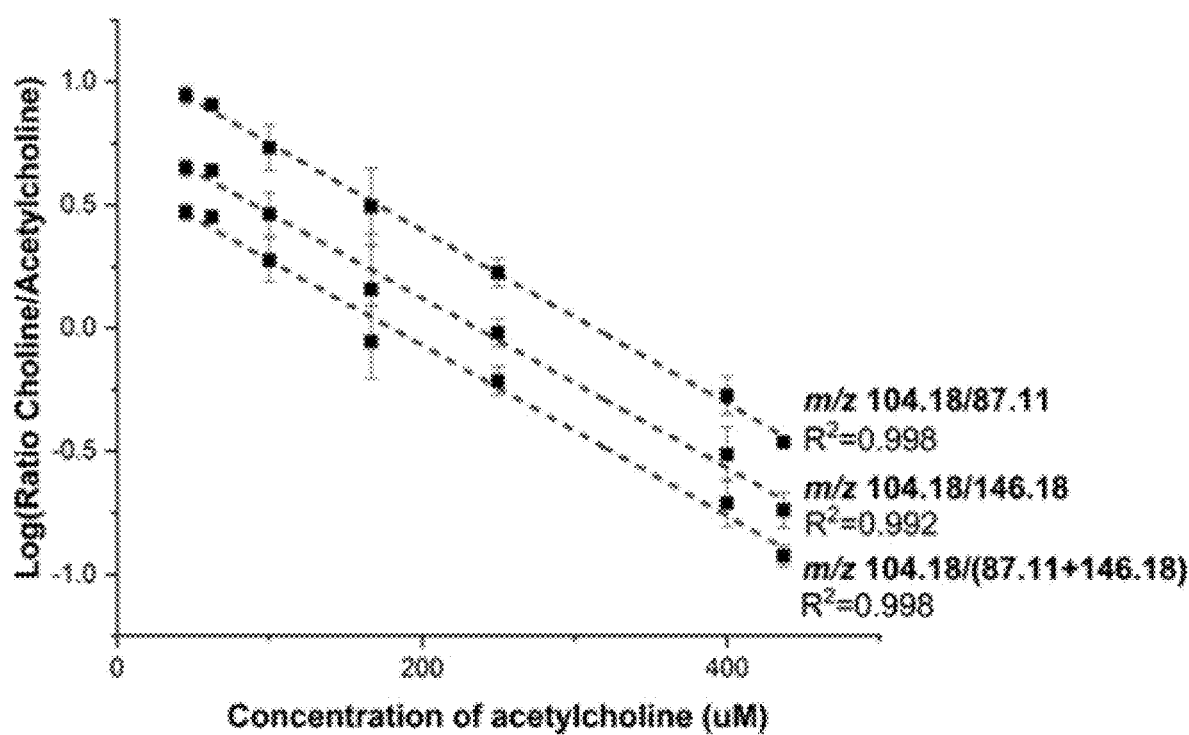
FIG. 15A shows simulated log-inhibition plot used to assess the performance of the approach using a different mass spectrometer (Waters QToF).
Figure 15B:
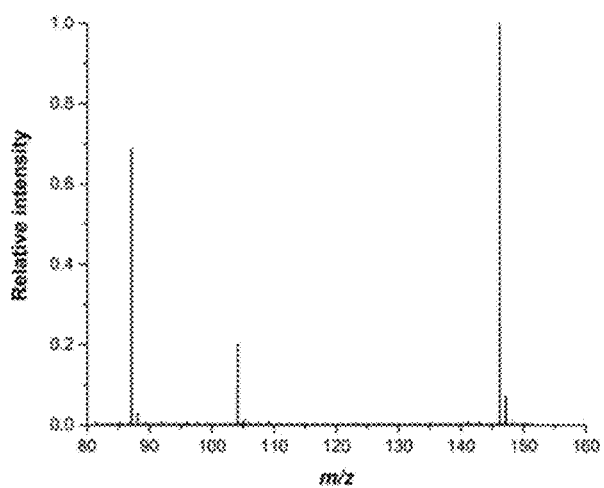
FIG. 15B shows a typical spectrum obtained with our approach using the QToF instrument.

FIG. 15A shows simulated log-inhibition plot used to assess the performance of the approach using a different mass spectrometer (Waters QToF). Data were acquired in a similar fashion to FIG. 14 panels A-B. Three plots (with statistically identical slopes) were obtained by using three different ratios of enzyme to substrate. These ratios were calculated using the intensity of choline (m/z 104) divided by either the molecular ion of acetylcholine (m/z 146), its fragment (m/z 87) or the sum of both (m/z 146+87). Results behave as expected. FIG. 15B shows a typical spectrum obtained with our approach using the QToF instrument.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A system for analyzing one or more enzymatic reactions, the system comprising:
a fluid handling system that includes a pinning device configured to interact with a microwell plate and prepare a plurality of discrete spots on a substrate, wherein each of the discrete spots comprises a substrate and a product of one or more enzymatic reactions, wherein both of the substrate and the product of the one or more enzymatic reactions are label-free;
an ionization source configured to direct sequentially a discharge from the ionization source onto each of the plurality of discrete spots to sequentially desorb the substrate and/or product from each of the discrete spots and sequentially generate ions of the substrate and/or product from each of the discrete spots;
a mass spectrometer positioned to receive the generated ions of the substrate and/or product from each of the discrete spots and analyze sequentially the ions of the substrate and/or product from each of the discrete spots in the mass spectrometer to thereby analyzing the one or more enzymatic reactions; and
a single control system that comprises one or more processors that control and coordinate the fluid handling system, the ionization source, and the mass spectrometer, such that the system is a fully integrated singular system and wherein one of the one or more processors is for determining whether the test compound inhibits the enzymatic reaction based on monitoring of the progress of the enzymatic reaction.

2. The system of claim 1, wherein the ionization source is a desorption electrospray ionization probe (DESI) and the discharge is a DESI spray.

3. The system of claim 1, wherein a subset of each of the plurality of the discrete spots further comprises a same test compound.

4. The system of claim 1, wherein the control system further determines how completely the test compound inhibits the enzymatic reaction based on the monitoring of the progress of the enzymatic reaction.

5. The system of claim 4, wherein the enzymatic reaction is associated with a physiological condition and determining how completely the test compound inhibits the enzymatic reaction determines whether the test compound should be considered for development into a drug to treat the condition.

6. A system for analyzing one or more enzymatic reactions, the system comprising:
   a fluid handling system that includes a pinning device configured to interact with a microwell plate and prepare a plurality of discrete spots on a substrate, wherein each of the discrete spots comprises a substrate and a product of one or more enzymatic reactions, wherein both of the substrate and the product of the one or more enzymatic reactions are label-free;
   an ionization source configured to direct sequentially a discharge from the ionization source onto each of the plurality of discrete spots to sequentially desorb the substrate and/or product from each of the discrete spots and sequentially generate ions of the substrate and/or product from each of the discrete spots;
   a mass spectrometer positioned to receive the generated ions of the substrate and/or product from each of the discrete spots and analyze sequentially the ions of the substrate and/or product from each of the discrete spots in the mass spectrometer to thereby analyzing the one or more enzymatic reactions; and
   a single control system that comprises one or more processors that control and coordinate the fluid handling system, the ionization source, and the mass spectrometer, such that the system is a fully integrated singular system wherein a subset of each of the plurality of the discrete spots further comprises an inhibitor of an enzyme of the enzymatic reaction and a test compound and wherein one of the one or more processors determines whether the test compound can counteract the inhibitor and re-start the enzymatic reaction.

7. The system of claim 6, wherein one of the one or more processors determines how completely the test compound counteracts the inhibitor and how completely the enzymatic reaction re-started based on the monitoring of the progress of the enzymatic reaction.

8. The system of claim 7, wherein one of the one or more processors determines how completely the test compound counteracts the inhibitor and how completely the enzymatic reaction is re-started determines whether the test compound should be considered for development into a drug that counteracts the inhibitor.

9. The system of claim 1, wherein each of the plurality of discrete spots is from a different time point in an enzymatic reaction.

* * * * *